(12) United States Patent
Raniere (10) Patent No.: US 7,041,049 B1
(45) Date of Patent: May 9, 2006

(54) SLEEP GUIDANCE SYSTEM AND RELATED METHODS

(75) Inventor: Keith Raniere, Clifton Park, NY (US)

(73) Assignee: First Principles, Inc., Clifton Park, NY (US)

( * ) Notice: Subject to any disclaimer, the term of this patent is extended or adjusted under 35 U.S.C. 154(b) by 29 days.

(21) Appl. No.: 10/718,960

(22) Filed: Nov. 21, 2003

(51) Int. Cl.
*A61M 21/00* (2006.01)

(52) U.S. Cl. .................. 600/26; 600/544; 128/905

(58) Field of Classification Search ............ 600/26–28, 600/544–546; 128/905
See application file for complete search history.

(56) References Cited

U.S. PATENT DOCUMENTS

| | | | |
|---|---|---|---|
| 3,884,218 A * | 5/1975 | Monroe | 600/28 |
| 4,444,199 A | 4/1984 | Shafer | |
| 4,454,886 A | 6/1984 | Lee | |
| 4,928,090 A | 5/1990 | Yoshimi et al. | |
| 5,167,610 A * | 12/1992 | Kitado et al. | 600/26 |
| 5,313,937 A | 5/1994 | Zdrojkowski | |
| 5,356,368 A * | 10/1994 | Monroe | 600/28 |
| 5,458,137 A | 10/1995 | Axe et al. | |
| 5,613,498 A * | 3/1997 | Yasushi et al. | 600/544 |
| 5,634,939 A | 6/1997 | Kuster et al. | |
| 5,662,117 A | 9/1997 | Bittman | |
| 5,771,261 A | 6/1998 | Anbar | |
| 5,899,867 A | 5/1999 | Collura | |
| 5,902,250 A | 5/1999 | Verrier et al. | |
| RE36,348 E | 10/1999 | Carter et al. | |
| 6,026,322 A | 2/2000 | Korenman et al. | |
| 6,042,548 A | 3/2000 | Giuffre | |
| 6,062,216 A | 5/2000 | Corn | |
| 6,078,549 A | 6/2000 | Wyatt et al. | |
| 6,085,747 A | 7/2000 | Axe et al. | |
| 6,102,846 A | 8/2000 | Patton et al. | |
| 6,102,847 A | 8/2000 | Stielau | |
| 6,132,384 A | 10/2000 | Christopherson et al. | |
| 6,175,762 B1 | 1/2001 | Kirkup et al. | |
| 6,188,927 B1 | 2/2001 | Lu et al. | |
| 6,210,355 B1 | 4/2001 | Edwards et al. | |
| 6,238,422 B1 | 5/2001 | Van Oort | |
| 2002/0080035 A1 * | 6/2002 | Youdenko | 340/573.1 |
| 2003/0231495 A1 * | 12/2003 | Searfoss, III | 362/251 |

* cited by examiner

*Primary Examiner*—John P. Lacyk
(74) *Attorney, Agent, or Firm*—Schmeiser, Olsen & Watts (57) ABSTRACT

A sleep efficiency monitor and methods for pacing and leading a sleeper through an optimal sleep pattern. Embodiments of the present invention include a physiological characteristic monitor for monitoring the sleep stages of a sleeper, a sensory stimulus generator for generating stimulus to affect the sleep stages of a sleeper, and a processor for determining what sleep stage the sleeper is in and what sensory stimulus is needed to cause the sleeper to move to another sleep stage. A personalized sleep profile may also be established for the sleeper and sleep guided in accordance with the profile parameters to optimize a sleep session. By providing sensory stimulus to a sleeper, the sleeper may be guided through the various sleep stages in an optimal pattern so that the sleeper awakens refreshed even if sleep is disrupted during the night or the sleeper's allotted sleep period is different than usual. Embodiments of the invention also involve calibration of the sleep guidance system to a particular sleeper.

20 Claims, 3 Drawing Sheets

SLEEP GUIDANCE SYSTEM AND RELATED METHODS

BACKGROUND OF THE INVENTION

1. Technical Field

This invention generally relates to sleep efficiency devices, and more specifically to a device and method for monitoring a person's sleep patterns through the person's physiological characteristics, determining an efficient sleep pattern, establishing a rapport between the person and a sleep guide, and guiding the person through one or more sleep patterns.

2. Background Art

Research indicates that a healthy adult sleeps an average of 7.5 hours each night and that most people sleep between 6.5 and 8.5 hours per night. Scientists do not know every facet of the sleeping process. However, researchers have determined that the sleeping process is a predictable cycle whose intervals are observable and may be monitored and examined clinically with polysomnography. Polysomnography provides data regarding electrical and muscular states during sleep.

Tracking the brain waves of sleepers using electroencephalographs (EEGs), researchers have currently identified and labeled six stages of sleep (including a pre-sleep stage), each stage characterized by distinctive brain-wave frequencies and patterns, as well as other physiological characteristics. Stage 0 is the pre-sleep stage and is characterized by low amplitude, high frequency alpha waves in the brain. At this stage, a person becomes relaxed, drowsy, and closes their eyes. Stages 1 through 4 are sometimes called non-rapid eye movement sleep ("NREM" sleep). Stage 1 is characterized by the sleeper's eyes rolling, and rhythmic alpha waves which give way to irregular theta waves that are lower in amplitude and have a lower frequency as the person loses responsiveness to stimuli. Stage 1 may last for five or ten minutes. Stage 2 is characterized by slower, larger brain waves punctuated by high frequency bursts of brain activity called sleep spindles which are marked by muscle tension. Stage 2 sleep is accompanied by a gradual decline in heart rate, respiration and temperature as the body prepares to enter deep sleep. Stages 3 and 4 normally occur 30 to 45 minutes after falling asleep. In Stage 3, there are fewer sleep spindles, but high amplitude and low frequency delta waves appear. Stage 4 is characterized by the high amplitude and low frequency delta waves appearing more than 50 percent of the time. The delta waves identify the deepest levels of sleep, when the heart rate, body temperature, respiration and blood flow to the brain are dramatically reduced, and growth hormones are secreted in the body. A person roused from Stage 4 sleep will be groggy and confused. Altogether, it takes between 30 and 120 minutes to complete NREM sleep. The pattern of the normal sleep cycle is: Stage 1, 2, 3, 4, 3, 2, Rapid Eye Movement Sleep. This cycle may repeat (often omitting Stage 1 during subsequent cycles), until a sleeper is awakened or sleep is disrupted. If the sleeper returns back to sleep, the stages may begin again, failing to complete the cycle.

Rapid eye movement sleep ("REM" sleep) makes up about 20 percent of sleep time. After REM sleep has begun, it is interspersed with NREM sleep every 30 to 40 minutes through the night. It is during REM sleep that dreams are experienced. In the REM sleep stage, the same fast frequency, low-amplitude beta waves that characterize waking states occur, and a person's physiological signs—heart rate, breathing, and blood pressure—also resemble those in the waking state. However, muscle tone decreases to the point of paralysis, with sudden twitches, especially in the face, hands and legs. REM sleep periods may last from 10 minutes at the beginning of a sleep cycle to one hour at the end of it.

Research has found that most people complete four to six complete sleep cycles each night, with each cycle lasting about 90 to 100 minutes. These cycles vary in composition, however; early in the night most of the time is spent in Stage 3 and 4 sleep, with Stage 2 and REM sleep predominating later on. Sleep patterns also may vary in the course of a person's life. On the average, an infant sleeps about 16 hours a day, in contrast to a 70-year-old who sleeps only about six hours a day. While REM sleep comprises about half of total sleep at birth, it eventually decreases to only about 25 percent of total sleep in old age. Sleeping patterns also vary greatly among individuals, and even among different cultures (in terms of napping, for example).

Regardless of the optimal sleep cycle or pattern for any particular person, many people have difficulty sleeping, are awakened in the middle of a sleep cycle, or otherwise do not have optimal sleep or do not use their sleep time as well as they could. To overcome sleep-related problems, many sleepers take sleep inducing or assisting drugs, attend psychological therapy, try relaxing techniques prior to sleeping, or just deal with not sleeping well. Many other sleepers do not realize they are not sleeping well and are, nonetheless, suffering the consequences of inefficient sleep. It would be advantageous to many sleepers to have a method for obtaining efficient sleep periods regardless of the person, their environment, and the time available for sleep.

DISCLOSURE OF THE INVENTION

The present invention relates to sleeping and methods and apparatus for obtaining efficient sleep and using sleep time more productively. Through the principles of pacing and leading, a rapport may be established with a sleeper's unconscious to cause the sleeper to transition through the various stages of sleep. As used herein, the term "stage" as it refers to stages of sleep is intended to refer not only to the six stages of sleep referred to in the current popular sleep literature, but also is intended to refer to and include all forms of recognizable sleep states, stages and patterns as well as physiological characteristic patterns that a particular sleeper may experience on a regular basis. When a person sleeps, whether categorization of that sleep is simplified into six stages common to all sleepers or is left more complex stages personal to the sleeper, the person's physiological characteristics illustrate recognizable patterns for that person. These patterns identify what portion of the person's sleep patterns the person is in. It is to distinguish the sleep portions by these recognizable and measurable patterns for the sleeper that "stage" is being used herein.

Embodiments of the invention include a processor coupled to various peripherals such as one or more physiological characteristic monitors, one or more sensory stimuli generators, memory, printers, displays and other inputs and outputs. By monitoring select physiological characteristics of the sleeper, it can be determined which sleep stage the sleeper is in, when the sleeper transitions to a different sleep stage, and whether a sleeper is following the lead of the sleep guidance system. One or more sensory stimuli are generated to lead the sleeper through the various sleep stages in an efficient manner. Processors of embodiments of the invention may be configured to receive a desired sleep period duration, calculate an efficient sleep cycle for the sleeper, and guide the sleeper through the efficient sleep cycle by monitoring the physiological characteristics of the sleeper and generating appropriate sensory stimuli to lead the sleeper to one or more desired sleep stages at the desired rate determined by the processor to meet the needs of the sleeper and or other criteria.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

Embodiments of the present invention relate to sleeping and achieving efficient sleep periods even when there is only little sleep time available, when the sleep period is interrupted, and when the sleeper has a particular time at which the sleeper wishes to wake up. By using the methods and apparatus configured according to embodiments of the present invention, a sleeper may be able to enjoy more efficient sleep, wake feeling more refreshed, and require less sleep than without the present invention.

Each person has particular sleeping habits and particular physiological characteristic patters indicative of the person's sleep. Some people may get by on three to four hours of sleep, while others may need nine or ten hours to feel refreshed. The right amount of sleep is whatever leaves the person feeling rested and alert. When sleep is interrupted, feelings of fatigue and irritability may be present the following day. Many people have difficulty falling asleep, are easily wakened from sleep, and otherwise have inefficient sleep resulting in feelings of fatigue or exhaustion, an inability to concentrate, and difficulty staying awake during the day. Because a sleeper cannot consciously control which stage of sleep the sleeper is in at any given time or how long the sleeper will remain in a particular sleep stage, many sleepers are experiencing frustration and fatigue relating to inefficient sleep patterns.

In public speaking, therapy and hypnosis, the principles of pacing and leading are commonly used as a way of establishing a rapport with an audience or subject to assist the person in changing to a different attitude or emotional state. By example, pacing in public speaking, in its most simple form, is matching or mimicking what the audience is doing at the time. This may involve matching some characteristic of the audience like the audience's attitude, mood, noise level, or level of excitement. Leading in public speaking is what the speaker says or does that is intended to get the audience to change its state of mind, attitude or level of excitement. If the audience follows the lead, the speaker may have an affect to change the audience in a way desired by the speaker. By first pacing the audience, the speaker can more easily, and often without the audience consciously being aware of it, change a characteristic of the audience. In this way, pacing and leading work together as tools for enhancing effective public speaking.

Through a pacing and leading model in communications, speakers have been found to more readily establish a rapport with their audience. For example, if a client sits with crossed legs and is leaning back and a professional does something similar, then the two are able to establish a level of understanding. If a client talks in visual terms and makes gestures in the air, or speaks rapidly, then a professional will be able to explain things much better and get along better with the client if the professional does the same. The rapport established through pacing and leading is generally understood to be more sub-conscious than conscious.

Pacing and leading is a form of behavioral conditioning which works on animals as well as humans. In a well known example of behavioral conditioning, Russian scientist Ivan Pavlov (1849–1936) discovered that by producing a common stimulus each time his test subject dogs were fed, he was later able to cause the dogs to salivate even when the dogs were not being fed by merely producing the same stimulus, i.e. a bell or a white lab coat. In other words, by pacing the dogs with a stimulus each time the dogs salivated, Pavlov was then able to lead the dogs to salivate with the same stimulus. This example illustrates the effect that prolonged pacing and leading can have on a subject.

Leading is not a cognitive process; the subject is not consciously being lead. When sensory stimuli is linked to the physiological characteristics of the person and the sensory input changes, the physiological response changes. For sleep patterns, once the particular physiological characteristics and patterns of the subject are known and to which stimuli the subject responds are known, the proper stimuli can be provided to the sleeper at appropriate times during sleep to affect the sleeper's sleep patterns.

Figure 1:
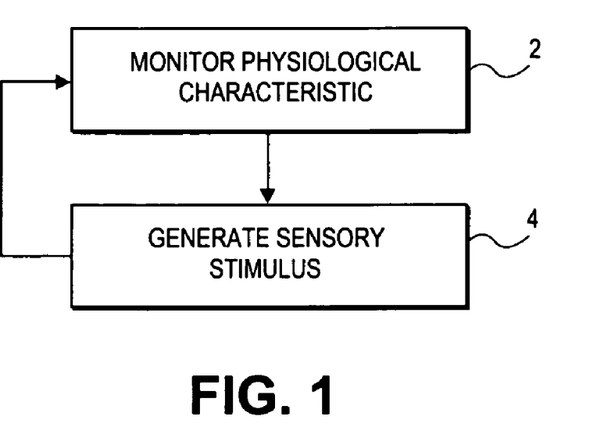
FIG. 1 is a flow diagram of a simple method of guiding a sleep pattern of a sleeper.

Embodiments of the present invention apply the methods of pacing, leading and behavioral conditioning to sleep patterns and cycles. FIG. 1 illustrates a first method of guiding a sleep pattern of a sleeper. As an initial step in guiding the sleep pattern of a sleeper, one or more physiological characteristics of the sleeper are monitored (Step 2). There are many physiological characteristics measured in the art that may identify in which sleep stage a sleeper resides at any given time. By measuring and monitoring one or more of those physiological characteristics, researchers are currently able to determine what sleep stage a sleeper is in, and when that sleeper has changed or will change to a different sleep stage. Accordingly, an appropriately configured processor may also be programmed to recognize the sleep stages and changes between them using well-known pattern recognition techniques. Examples of physiological characteristics which are currently known to be indications of sleep stages include, but are not limited to, the sleeper's: heart rate, pulse rate, blood pressure, brain wave patterns, muscle tension, eye movement, noises, loudness of noises, body position, body movement, rate of body movement, respiration, respiratory effort, respiratory airflow, body temperature, blood flow, blood oxygen level and blood chemistry. Appropriate sensors and equipment for monitoring each of these physiological characteristics are well known in the art and are available from a variety of manufacturers such as Philips Medical Systems of The Netherlands, Hewlett-Packard of Palo Alto, Calif., and Elixa of Albuquerque, N. Mex.

In simple embodiments of the invention, once it is determined that a person is within a particular sleep stage, a sensory stimulus may be generated or one or more characteristics of existing sensory stimuli may be altered (Step 4)

to lead the person toward another sleep stage. Sensory stimuli may be any stimuli that can be sensed by sleeper. For example, and without limitation, sensory stimuli may include light, sound, smell, vibration, heat or cold, moisture, electric shock, adjustments to the sleeper's bed hardness or angle, or, even changes in air flow such as a breeze or air content such as oxygen levels, and anything else that can be sensed by a sleeper. Adjustments which may be made to sensory stimuli to lead the sleeper toward another sleep stage may include, but are not limited to, adjustments in the magnitude or quantity, tone, quality, pattern, frequency, angle, composition, source location, application location or any other adjustment to sensory stimuli, however small, which can be sensed by a sleeper.

The following is a specific application of the invention for exemplary purposes only. A sleeper's brain wave pattern, or other physiological characteristic, may be monitored to determine the sleep stage in which the sleeper resides. With appropriate conditioning, as described more fully below, when the brain waves reflect that the sleeper is in a particular stage of sleep, for example Stage 1 sleep, an appropriate auditory tone of a predetermined frequency, volume and/or pattern may be generated by an appropriate source. The auditory tone is used to pace the sleeper by establishing a rapport with the sleeper's subconscious. Changes in the tone, such as by changing the frequency with which it chimes, is then used to lead the sleeper to the sleeper's next consecutive sleep stage, in this example Stage 2 sleep, or to lead the sleeper to take on certain physiological characteristics.

This process may continue, using the same or different auditory tones or other stimuli, to lead a sleeper through various sleep stages throughout the sleep period in an optimal manner, each time establishing a rapport and leading the sleeper through sleep. By continuously monitoring the current sleep stage and physiological characteristics of the sleeper while it is leading the sleeper through the sleep stages, a sleep guidance system configured according to embodiments of the present invention can adapt a sleeper's sleep pattern for efficient sleep even when sleep is disrupted. The transition from NREM sleep to REM sleep and back again is important to the sleeper feeling refreshed and the sleeper's body being rejuvenated. Accordingly, particular embodiments of the invention may alternatively be configured to focus primarily upon broadly monitoring the physiological characteristics of NREM and REM sleep and generating sensory stimuli to pace and lead a sleeper to enter REM sleep from NREM sleep, or any other categorization of sleep stages, and to return to NREM sleep from REM sleep at appropriate times.

Figure 2:
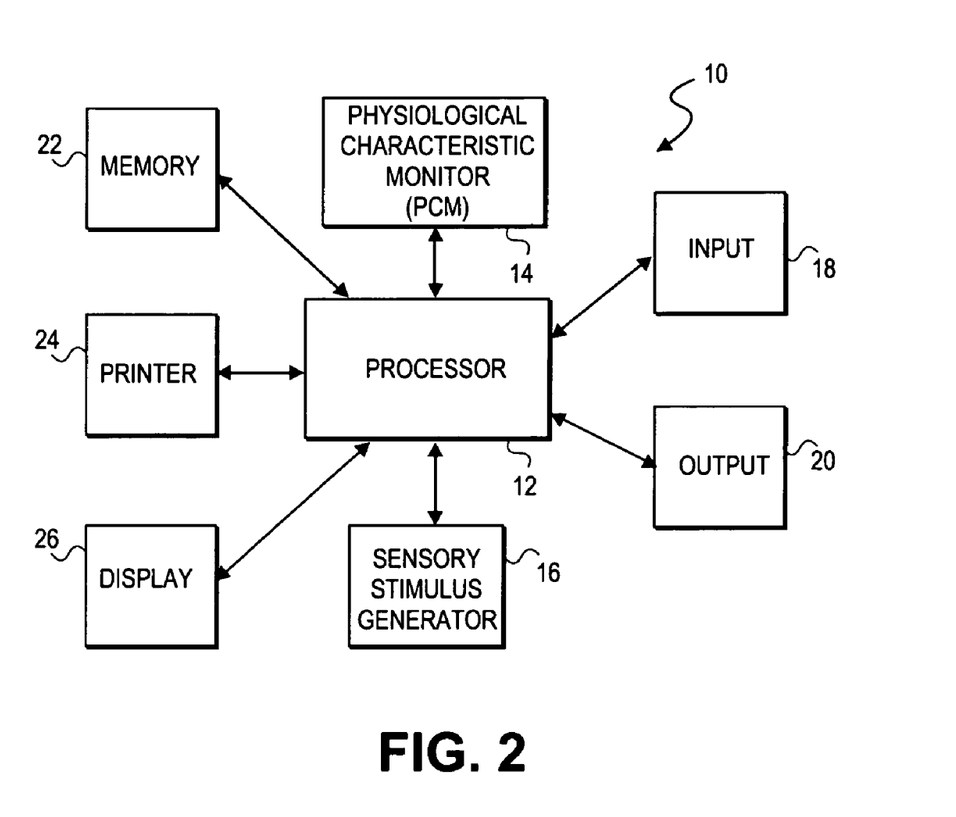
FIG. 2 is a block diagram of a sleep guidance system configured according to an embodiment of the present invention.

FIG. 2 illustrates an exemplary system 10 to implement the methods for embodiments of the present invention. The system 10 illustrated in FIG. 2 includes a processor 12 configured, through hardware, software or both, to communicate with each of a number of associated peripherals. It will be understood by those of ordinary skill in the art that the processor 12 may comprise a single processor 12, or may be divided into two or more processors 12 and that the processor 12, through the peripherals coupled to the processor 12, controls the operations of the sleep guidance system and leads the sleeper through sleep. The processor 12 may be configured differently for each embodiment of the invention to coordinate and enable the various establishing of a sleeper profile, monitoring of physiological characteristics, interpreting of the physiological characteristic data received, mapping the sleep patterns and physiological characteristics of the sleeper throughout the sleep cycle, determining of a sleeper's current sleep stage, identifying of which physiological characteristics indicate when a sleeper is about to transition to a new sleep stage and which sensory stimuli characteristics will pace and lead the sleeper to transition to a new sleep stage, and generating of sensory stimuli to pace and lead the sleeper to the new sleep stage.

Any number of conventional and unconventional peripherals may be operatively coupled to the processor 12 to assist in carrying-out the various embodiments of the invention. For example, one or more physiological characteristic monitors (PCMs) 14 may be coupled to the processor for monitoring a sleeper. PCMs may include any device configured to detect any physiological characteristic. Some specific examples of these include, but are not limited to, electrooculograms, electromyograms, electroencephalographs and other polysomnography monitors, microphones, motion sensors, moisture sensors, muscle tension monitors, blood pressure cuffs, respirators, pulse oximeters, thermometers, and the like, and any other sensor that can detect a physiological characteristic of the sleeper.

A sensory stimulus generator 16 is also operatively coupled to the processor 12 to communicate with the processor 12 in providing sensory stimuli to the sleeper. The sensory stimulus generator 16 may include any device configured to generate any stimulus which may be perceived by the sleeper through the sleeper's senses. Some specific examples of devices configured to generate stimuli include, but are not limited to, speakers, vibrators, lights, electric contacts, fans, heaters, coolers, and the like. The precise configuration of the sensory stimulus generator 16 may take many forms, but may include such forms as: ear phones, a mask, a headband, a belt, a wristband, a ring, a wall mounting and any other generator, including those configured to generate stimuli from a remote location such as an end table, a cabinet or an extension arm near the sleeper.

Other inputs 18 and outputs 20 may also be included to assist in interacting with the processor 12 or for receiving data from the processor 12. It is anticipated that in certain embodiments of the invention, a personal computer running Microsoft Windows operating software may be used as the processor and be coupled to various peripherals to function as the sleep guidance system. In other embodiments, other operating systems, programming languages, or even merely machine code may be used. Memory 22 is also included, such as RAM and/or ROM, to enable storage of data. Additional memory 22 may also be included such as backup memory, memory storage devices such as compact or digital video disc memory, magnetic media memory or any other memory conventionally used with computers for storing data. A printer 24 and display 26 may also be provided.

As will be clear to those of ordinary skill in the art, embodiments of a sleep guidance system according to the invention may be configured to include expensive equipment and processes which may only practically be available through a sleep clinic, or any other medical facility, or may be more simply configured with less expensive equipment for personal home use. For example, while electroencephalographs can often identify the precise sleep period of a sleeper more accurately than a pulse oximeter, the cost of an electroencephalograph can be much greater than that of a pulse oximeter. Accordingly, it will be clear to those of ordinary skill in the art reviewing this disclosure that certain processes explained herein may be performed with much greater accuracy and obtaining faster results using more accurate or specialized polysomnography equipment. It is not crucial to the invention which particular model or brand of peripheral or processor is used in embodiments of the invention. One of ordinary skill in the art will readily be able to select and utilize appropriate components for a sleep guidance system from the disclosure herein.

Figure 3:
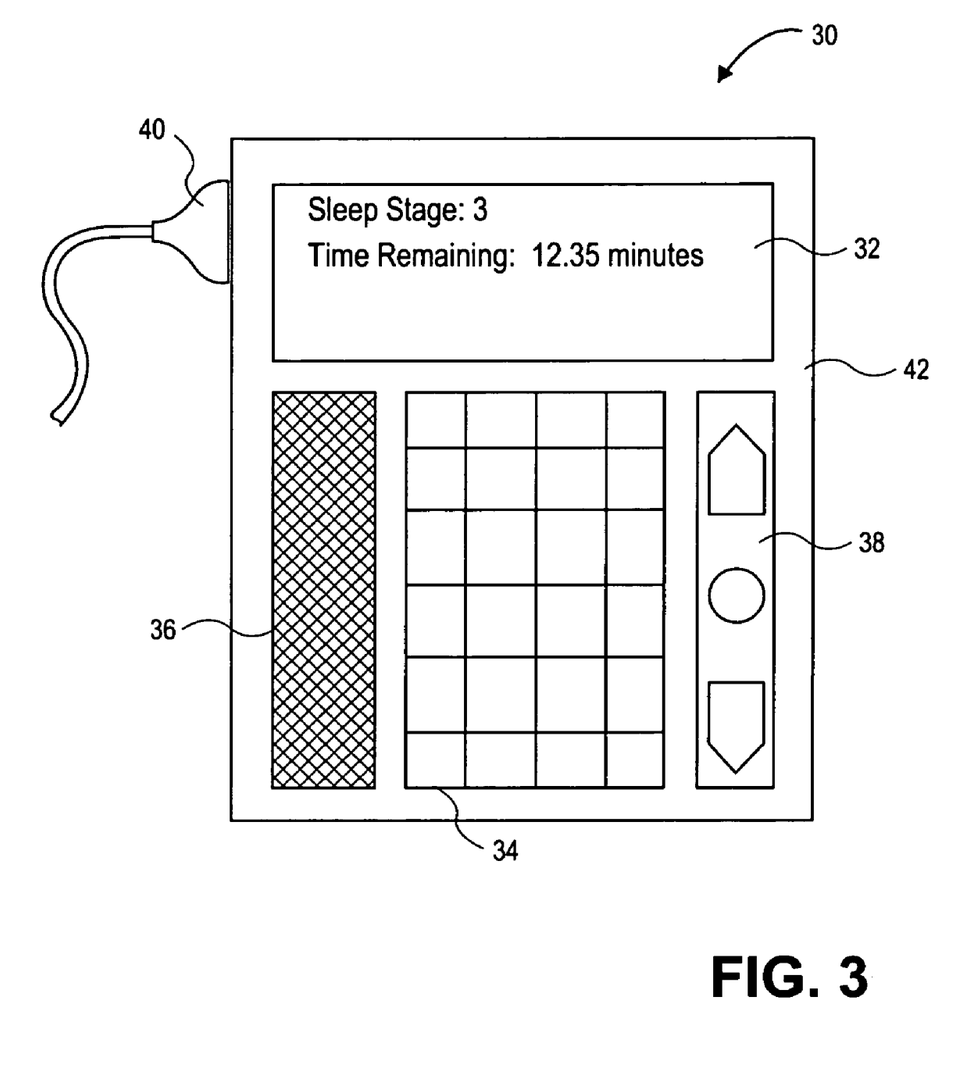
FIG. 3 is a top view of a sleep guidance system configured according to an embodiment of the present invention.

FIG. 3 illustrates a simpler embodiment of a sleep guidance system of the present invention. The system 30 of FIG. 3 includes a display 32, input keypad 34, speaker 36, scroll bar 38 and an input and/or output plug 40. Though not specifically illustrated, a processor (such as that shown in FIG. 2) and other related hardware and software is included within the housing 42 of the system 30. The display 32 may be any display commonly used for electronics such as liquid crystal, light emitting diode, laser diode, plasma, any touch sensitive display, and the like. The input keypad 34 and scroll bar 38 may be any keypad or touchpad technology known in the art which allows a user to input commands to a processor. Similarly, the particular speaker 36 used is not crucial to the invention. The input and/or output plug 40 may be any connection between the processor and a peripheral device. In particular embodiments of the invention, for example, a serial or parallel data cable such as that conventionally used between a personal computer and a peripheral may be used. The input and/or output plug 40 of the present embodiment is configured to couple to a PCM monitoring a sleeper. Alternatively, wireless PCMs and stimulus generators may be used to reduce the likelihood that the sleeper will become tangled in a wire and have sleep disrupted by a PCM or stimulus generator attached to the sleeper. The use of wireless PCMs and sensory stimulus generators have particular advantage in embodiments of the present invention because they reduce the risk of disrupting the sleeper. Wireless communication technologies are well known in the art. Some examples of wireless communication technologies which may have particular application with the present invention include, but are not limited to, Bluetooth technologies, WiFi, cellular technologies, radio wave technologies, red and infrared technologies, and technologies using other frequencies of communication signals whether encoded or unencoded, or mixed with other carrier signals or not.

In a more complex embodiment of the present invention, a processor with peripherals, such as that shown in FIG. 2 or 3, is configured to perform one or more portions of the method shown and described with reference to FIG. 4. Hardware and software developers of physiological characteristic monitors will understand how to appropriately configure the sleep guidance system of embodiments of the invention to accomplish the methods described below using hardware solutions, software solutions, or more likely a combination of both.

Figure 4:
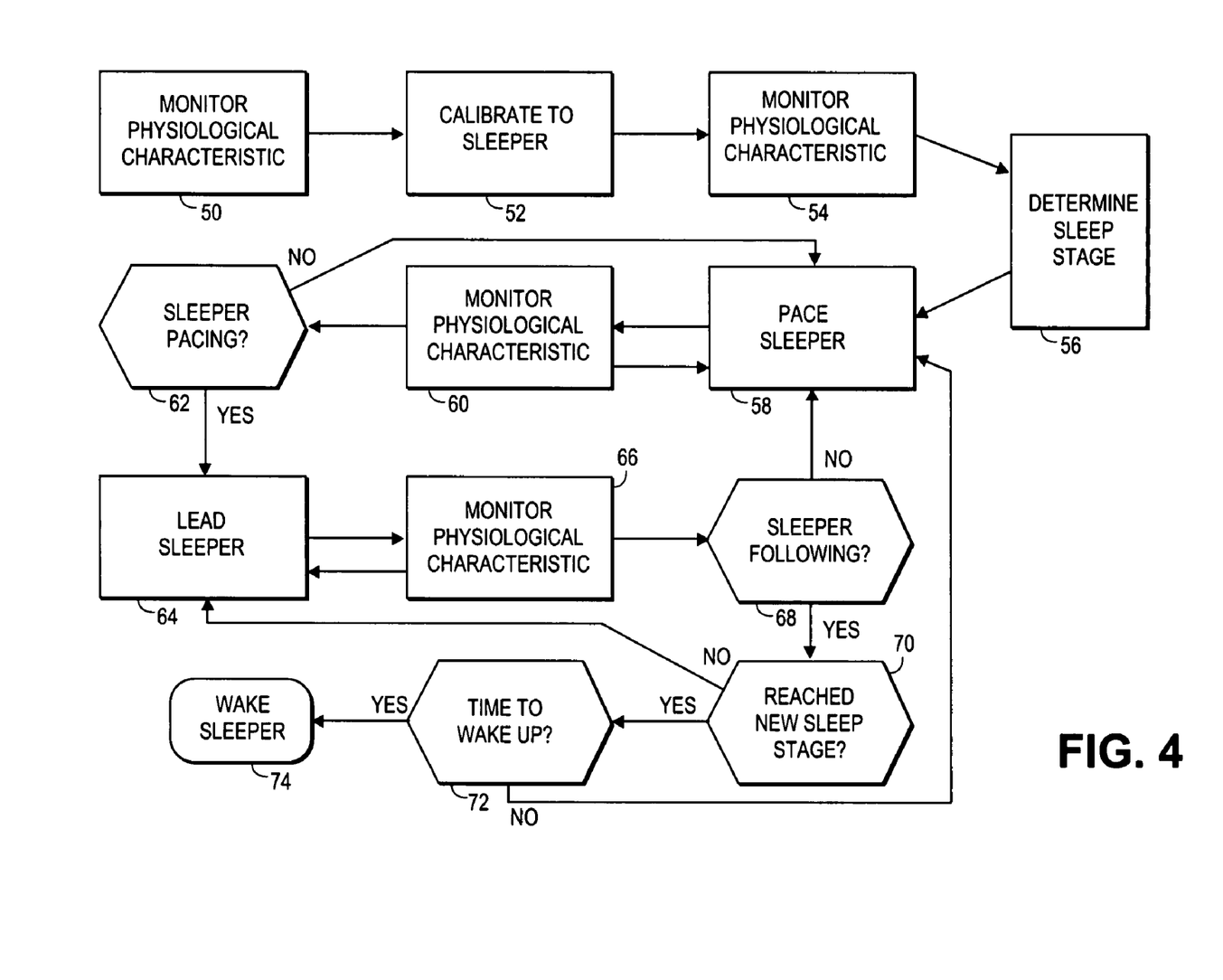
FIG. 4 is a flow diagram of a more complex method of guiding a sleep pattern of a sleeper.

According to the embodiment of the method of guiding the sleep stages of a sleeper shown in FIG. 4, one or more physiological characteristics of a sleeper are monitored by an appropriately configured processor through a PCM (Step 50). As explained previously, by monitoring the physiological characteristics of a sleeper, it may be determined not only in which sleep state a sleeper resides, but what physiological characteristics of the particular sleeper best indicate that the sleeper is about to transition to a particular sleep stage and which sensory stimuli is effective to lead the sleeper to a particular sleep stage. In this way, a personalized sleeper profile may be established for the sleeper and stored in association with the processor. The profile may include any of the following, without limitation, information indicative of the sleeper's sleep stages, physiological characteristics to indicate particular sleep stages and transitions between sleep stages, and stimuli settings to pace and lead the sleeper through sleep.

For example, one person may evidence one particular brain wave pattern or a particular frequency of brain wave peaks while transitioning to REM sleep, and another person may evidence a different brain wave pattern or a different frequency of brain wave peaks. As another example, a first person may have a significant change in heart rate and little noticeable change in respiration throughout Stage 2, while a second person may have a smaller change in heart rate and a greater noticeable change in respiration. Additionally, one sleeper may respond more readily to noise or even verbal instructions during sleep to pace and lead the sleeper, and another sleeper may respond more readily to changes in ambient temperature or airflow. Thus, in certain embodiments of the invention, a sleep guidance system may be configured to monitor the physiological characteristics of a sleeper, to calibrate to the particular sleep patterns and physiological characteristics of a sleeper (Step 52), and to establish a personalized sleeper profile.

Calibration to a sleeper (Step 52) may involve merely monitoring the sleep patterns and/or physiological characteristics of a sleeper, or may additionally involve providing sensory stimuli to the sleeper to determine the sleeper's physiological and sleep pattern responses to those sensory stimuli during sleep. Calibration of a sleep guidance system to a sleeper may involve such steps as evaluating which physiological characteristics most clearly indicate a change between the sleeper's sleep stages, which patterns of physiological characteristics occur at which portions of the sleeper's sleep cycle or under which circumstances, how a sleeper's physiological characteristics or sleep patterns change when exposed to sensory stimuli, how a sleeper's physiological characteristics respond when; sleep is disrupted, optimal durations and patterns for a sleeper's sleep cycle, what sensory stimuli works most effectively to pace and/or lead the sleeper through the sleep stages, and recording these or data indicative of these in the sleeper's personalized sleep profile. Calibration involves any process that gathers information about the sleeper or sleeper's sleep patterns for use in personalizing the sleep guidance process to the particular sleeper. Many other processes may be used to calibrate the method to a particular sleeper.

By using a multi-dimensional space profile for the sleeper, known to those of ordinary skill in the mathematical arts, multiple variables may be tested and varied simultaneously to obtain an optimal combination of stimuli resulting in a variety of physiological characteristic responses. Depending upon the sleep characteristics most needed by the particular sleeper, the multi-dimensional space profile approach will allow the sleep guidance system to focus on particular sleep benefits needed by the sleeper and provide the pacing and leading techniques most effective with the sleeper. For example, a particular default or other established profile may be scaled for a particular sleeper, or by holding particular variables, such as sleep stage durations and the like, constant while others vary. The possible variations are many, and those of ordinary skill in the art will understand how to establish and maintain an appropriate personal profile for affecting the pacing and leading during a sleep session from the disclosure provided herein. It will also be understood by those of ordinary skill in the art from this disclosure that the various methods of the invention do not require calibration to the sleeper prior to attempting to pace or lead the sleeper. The personalized profile, including any number of variables, may be formed while the sleep guidance system is pacing and leading the sleeper, or may not even be used in certain embodiments depending upon the particular application of the invention and history of guidance with the particular sleeper. However, prior calibration and reference to the stored personalized sleep profile may provide better results than without calibration as explained more fully below.

When it is time for guiding a sleeper's sleep, one or more physiological characteristics of the sleeper are monitored (Step 54). If the sleep guidance system has been previously calibrated for the sleeper, the guidance system may be able to more easily monitor only one or two physiological characteristics for previously evaluated indicators of particular sleep stages. Nevertheless, at least one physiological characteristic of the sleeper may be monitored to determine in which sleep stage the sleeper resides (Step 56) based upon the data gathered while monitoring the physiological characteristic. Polysomnographers in the art are well versed in identifying and distinguishing between sleep stages for a sleeper based upon physiological characteristic data.

The particular sleep stage for the sleeper may optionally be determined (Step 56). The sleeper may be paced (Step 58) to begin establishing a rapport with the sleeper. As will be clear to those of ordinary skill in the art, it is not necessary to know the particular sleep stage of the sleeper, and there are instances where a predefined sleep stage may not exist. For example, sleep apnea is a common problem for some sleepers which does not allow the sleepers to obtain a good night sleep because the sleeper stops breathing for extended periods of time throughout the night. Sleep apnea sufferers often cannot enter deep sleep and have irregular sleeping stages because they wake up regularly throughout the night. Nevertheless, without knowing which actual sleep stage the sleeper is in, embodiments of the present sleep guidance system may be able to pace the sleeper's breathing or other physiological characteristic and lead the sleeper to enter a deeper sleep stage whatever the stage is. This can be accomplished, for example and without limitation, by detecting a physiological characteristic pattern that occurs before the apnea stage starts, and then leading the sleeper to a different physiological pattern out of the apnea pattern so that the sleeper does not experience the sleep apnea and, thus, is able to sleep better. As can be seen through this example, the stages referred to in this description are not limited to specific sleep stages, but more broadly include physiological characteristic patterns that can be monitored. By pacing and leading the sleeper, those physiological characteristic patterns may be altered to better utilize the sleeper's sleep time.

Three other examples of categories of nontraditional sleep stages relate to bedwetting, sleepwalking and nightmares. By monitoring one or more physiological characteristics of the sleeper (Steps 50 and 54), particular embodiments of the invention may be able to calibrate to the sleeper (Step 52) and determine the sleep stages (Step 56) characteristic of the sleeper about to wet the bed, begin sleepwalking or have a nightmare. Similar to the explanation of how the system would pace and lead a sleeper suffering from sleep apnea, it is not necessary to know a particular predefined sleep stage for the sleeper. The system need only be able to detect, recognize and respond to particular physiological characteristic patterns indicative of the sleeper entering a stage of sleep where undesired events are experienced. The sleeper may then be paced (Step 58) and lead (Step 64) to a different physiological pattern, out of the undesirable pattern, so that the sleeper does not experience the undesired events. As will be clear from the present disclosure, embodiments of the present invention may be used to help sleepers overcome a wide variety of problems that disrupt sleep. Several non-limiting examples have been provided herein, but those of ordinary skill in the art will readily be able to adapt the methods and apparatus disclosed herein to help sleepers overcome, or perhaps avoid, many sleep problems.

In a particular embodiment of the invention, the stimuli used to lead the sleeper is a human or synthesized human voice providing subliminal cues or suggestions to the sleeper. When a person is asleep, the person is more apt to follow suggestions than when awake. Some people are also more apt to follow suggestions than other people. During calibration of the system and establishment of a personalized profile for the sleeper, it is contemplated that particular embodiments of the invention will use verbal suggestions as stimuli to determine whether the sleeper may be paced and lead with verbal suggestions as well.

In another particular embodiment of the invention, verbal instructions are provided to the sleeper during particular sleep stages or when the sleeper is exhibiting particular physiological characteristics or patterns. During certain times of sleep, the sleeper can actually learn better or respond better to instruction than in other times of sleep. In the past, others have attempted to take advantage of this characteristic of sleepers by playing foreign language or other learning tapes while they sleep. Because the learning occurs best during only certain stages of sleep, however, much of the instruction provided during the other stages of sleep is lost. Embodiments of the present invention overcome this challenge by monitoring the physiological characteristics of the sleeper to determine when the sleeper is most likely to learn during sleep and providing the verbal instructions, or at least the most important verbal instructions, during that stage of the sleep. Because the guidance systems of the present invention can also pace and lead a sleeper to different stages of sleep, the system can actually lead the sleeper to an learning stage of sleep, provide verbal instructions for the sleeper, lead and maintain the sleeper within the learning stage for longer to ensure instruction is completed. The sleeper's learning stage of sleep may be determined during calibration and the appropriate data stored in the sleeper's personalized profile. As with any other embodiment of the present invention, the personalized profile may be updated and amended during subsequent use of the guidance system with the sleeper by noting the sleeper's responses and physiological characteristics. Those of ordinary skill in the art are familiar with the physiological characteristics exhibited during learning stages of sleep and will readily be able to employ and adapt the systems and embodiments disclosed herein for use in helping people learn in their sleep more efficiently.

Pacing may involve repeating a particular sensory stimulus each time a particular physiological characteristic is monitored. To determine whether the sensory stimuli is appropriately pacing the sleeper (Step 62), one or more physiological characteristics are monitored (Step 60). Throughout the examples and discussions provided herein, where referral is made to the monitoring of a physiological characteristic, it should be understood that those explanations may be applied equally to monitoring two or more physiological characteristics. While monitoring only one characteristic may be sufficient to practice the inventions described herein depending upon the sleeper, monitoring of multiple characteristics and the parametric monitoring of the multiple interactions and variances of those characteristics and their respective patterns, is expected to provide more detailed indications of transitions between sleep stages and of the effectiveness of the pacing and leading.

In one particular example of pacing, when a particular physiological characteristic threshold is detected, such as the sleeper drawing a breath, a sensory stimulus such as a short, quiet hum may be produced from a speaker such as the speaker 36 of FIG. 3 or the sensory stimulus generator 16 of FIG. 2. Each time the sleeper draws a breath, the short, quiet hum is produced. The hum is quiet enough to not disturb the sleeper's sleep, and short enough to be distinguishable from subsequent hums and create a subconscious, Pavlovian-like association between the sleeper's breath and the hum. After a time, for example 30–60 breaths, to determine whether the sleeper is pacing (Step 62), a characteristic of the hum, such as the volume, the frequency, the duration, or the timing, is adjusted slightly. The physiological characteristic is monitored (Step 60) to determine whether the adjusted hum characteristic had any effect on the sleeper's breathing. If, as anticipated, the adjusted hum characteristic caused a comparable adjustment to the sleeper's physiological characteristic, it may be presumed that the sleeper is pacing with the sleep guidance system. If not, the sleeper may be paced for a longer period of time, using the same, an alternative, or an additional physiological characteristic, using an alternative sensory stimuli, or with a different adjustment to the characteristic of the sensory stimuli.

In one specific example of how the invention may be applied, a particular sleeper is paced (Step 58) using a soft 60 Hz hum having a duration of 0.5 seconds for 30 breaths. For this sleeper, it was previously determined during calibration that this hum had the desired affect of pacing the sleeper. To determine whether the sleeper is pacing (Step 62), the hum is adjusted to a soft 50 Hz hum having a duration of 0.6 seconds for several additional breaths (e.g. 5–10), and the sleeper's breathing is monitored (Step 60). The necessary adjustments to the hum may be determined from trial and error, from experience in dealing with sleepers, or from the results of calibration tests on this particular sleeper. In this example, based upon calibration results, it may be anticipated that this change would cause the sleeper's breathing rate to slow. Regardless of the change that occurs in the sleeper, however, if the sleeper's breathing rate changes commensurate with the change in the characteristics of the hum, the sleeper is pacing with the sleep guidance system at some level and is being lead. Some sleepers may pace easily and require only a few or only less extreme sensory stimuli being generated to establish a rapport. Other sleepers may require sensory stimuli for a longer time or of greater magnitude to establish a rapport. A good indication of what sensory stimuli will best pace and lead a sleeper through sleep stages and what physiological characteristics indicate that the sleeper's sleep patterns are pacing and leading may be determined through calibrating the system to the sleeper either before pacing, or by gathering data during one or more sleep guidance sessions. Because each sleeper is different and may respond differently to each sensory stimulus provided or pattern of sensory stimuli provided, pre-calibrating a system to a particular sleeper may allow a rapport to be more quickly established between a sleeper and a sleep guidance system configured according to embodiments of the present invention. Establishing a personalized sleep profile for a sleeper is included in calibration of the system to the sleeper. This personalized sleep profile may be stored electronically, or otherwise, and transferred from one system to another. As part of calibrating a particular system to a sleeper (Step 52), the system may receive a sleeper's personalized profile from another computer system for use in pacing and leading the sleeper with the present system. By enabling an ability to transfer sleep profiles between systems, or for storage or archiving, a relatively complex system may be used to determine a sleeper's personal profile, perhaps in a sleep clinic for example, and a relatively less complex system, such as a remote portable system at the sleeper's home, may be used on a daily basis to help the sleeper sleep.

Once it is determined that a sleeper is pacing, the sleeper is ready to be lead (Step 64) to a different sleep stage. Leading involves adjusting a characteristic of the sensory stimuli being generated to cause a desirable change in a physiological characteristic of the sleeper. As with pacing, the precise sensory stimuli used to initiate a change in a physiological characteristic of the sleeper or to lead the sleeper to a new sleep stage may be determined through trial and error, through experience with other sleepers, or through data obtained during calibration. For example, if a sleeper is in Stage 2 sleep, characterized by a slowed heart rate and breathing, a particular sleeper may be lead through Stage 2 sleep to Stage 3 sleep, characterized by yet further slowed heart rate, further slowed breathing and relaxed muscles, by producing sensory stimuli having characteristics to initiate slower breathing. By specific example, this may involve adjusting the pacing "hum" described above very slightly over a predetermined time (i.e. 2–15 minutes) to gradually slow the breathing and heart rate of the sleeper to a rate characteristic of the sleeper's Stage 3 sleep. To determine whether the sleeper is following the leading (Step 68), at least one physiological characteristic is monitored (Step 66) while the sleeper is being lead (Step 64).

Once it is determined that the sleeper is following the lead (Step 68), the sleep guidance system, through monitoring the physiological characteristics of the sleeper, determines whether the sleeper has reached a new sleep stage (Step 70). This may be done by direct monitoring of the sleeper's brain waves or one or more other physiological characteristics of the sleeper indicative of the sleeper's sleep stage. If calibration was performed previously, the calibration data collected may allow the sleep guidance system to monitor physiological characteristics of the sleeper other than the brain waves to objectively determine that the sleeper is in a particular sleep stage. However, as will be clear to those of ordinary skill in the art, it is not required by the invention to specifically know which sleep stage the sleeper is in to pace and lead the sleeper. Nevertheless, if the sleeper has not reached a new sleep stage (Step 70) or recognized pattern of one or more physiological characteristics, the system continues to lead the sleeper (Step 64) until the new sleep stage has been reached (Step 70). If the sleeper has reached a new sleep stage (Step 70), the sleep guidance system determines whether it is time to wake up from sleep (Step 72). If so, the sleep guidance system may wake the sleeper (Step 74), or may merely permit the sleeper to wake naturally from a light sleep. If it is not time for the sleeper to wake (Step 72), the sleep guidance system may continue to either pace and/or lead a sleeper through another sleep stage or cycle. Alternatively, if the sleeper is at the final sleep stage (i.e. Stage 1 or 2) and it is only a short time until the sleeper is to wake, the sleep guidance system may pace and/or lead the sleeper through a longer final sleep stage until it is time to wake.

It is anticipated that select embodiments of a sleep guidance system of the present invention will be configured to allow a sleeper to select a sleep period duration and calculate the optimal time for each sleep stage and the number of sleep cycles to leave the sleeper in a final sleep stage at the end of the sleep period duration as an optimal sleep pattern for the sleeper. In this way, the sleep guidance system can customize the sleep cycle to the sleeper's needs based upon when the sleeper needs to be woken up rather than on the variable time at which the sleeper may fall asleep. By example, if a particular sleeper ordinarily sleeps for eight (8) hours and needs to wake up, instead, in four (4) hours, the sleeper may select the appropriate wake-up time and the system will optimize the sleeper's sleep throughout the night regardless of how long it takes the sleeper to fall asleep. Furthermore, if the sleeper's sleep is disrupted during sleep, the sleep guidance system may then recalculate the times for the sleep stages and the number of sleep cycles and continue guiding the sleeper through the revised optimal sleep pattern. By receiving feedback from the sleeper in the form of physiological characteristic responses, the sleep guidance system can adapt to a particular sleeper's sleeping habits and to any environment in which the sleeper may choose to sleep, providing the sleeper with optimal sleep for that sleeper in that environment.

It is also anticipated that each time a sleeper is guided by a sleep guidance system of the present invention, the sleeper will more readily pace with the sensory stimuli and follow it. It is contemplated that in embodiments of the invention, rather than pacing and leading using small physiological characteristics such as heart rate or breathing, pacing and leading may be performed on a larger scale. For example, it is believed that like Pavlov's dogs who were conditioned to salivate when they heard a bell, sleepers may be conditioned over time to change sleep stages in response to one or more selected sensory stimuli. In one particular embodiment, throughout standard pacing and leading as discussed above, or merely while monitoring a sleeper's natural sleep patterns, sensory stimuli are provided at selected points in a sleeper's sleep cycle, such as around transitions from one sleep stage to another or when a monitored physiological characteristic reaches a significant milestone or threshold of change for a sleep stage or sleep cycle. By producing the sensory stimuli at the same point of the sleep stage every time the sleeper reaches that point of the sleep stage, a sleeper may be conditioned to move to that point of the sleep stage with physiological characteristics indicative of that sleep stage in response to the sensory stimuli. In this way, the necessary sensory stimuli for guiding a sleeper through efficient sleep may be reduced over time.

In one particular embodiment of the invention, a sleep guidance system is calibrated to a particular sleeper in a sleep clinic using polysomnography equipment. The sleep guidance system may be calibrated to the sleeper by monitoring the sleeper's sleep patterns, corresponding physiological characteristics, and changes in the sleeper's physiological characteristics in response to selected sensory stimuli as discussed previously herein. The sleeper may also be paced and lead during numerous sleep cycles within the clinic to begin training the sleeper to sleep guidance and to refine calibration of the sleep guidance system data. Subsequently, the sleeper may use a home-version of the sleep guidance system that includes some polysomnography equipment for temporary home use to confirm that the sleeper is still training to the sleep guidance and that further calibration is not needed. The duration of use of the polysomnography equipment depends upon how readily the subconscious of a sleeper accepts the sleep guidance and how readily a rapport is established. Eventually, only a simple sleep guidance system may be needed which monitors only one or two physiological characteristics of the sleeper and paces and leads with only a single type of sensory stimulus, i.e. sound, light or vibration. As explained previously, the sleeper's personal sleep profile may be transferred between systems to simplify later calibration by relatively less complex systems.

As part of conditioning a sleeper to a sleep guidance system, multiple sensory stimuli may be used to cause a desired physiological response and to tie a sensory trigger to that response. For example, it is known that flashing lights into a person's eyes at certain frequencies will cause the person's brain waves to match the frequencies of the flashing lights. To help guide a sleeper through a sleep stage, flashing lights or other stimulus may initially be used as a primary stimulus to cause the sleeper's brain waves to match a desired frequency of a particular sleep stage at a point in a sleep cycle. The brain waves may be monitored by appropriate polysomnography equipment to determine whether the sleeper is pacing and being lead through sleep stages by the primary sensory stimulus of the lights. A secondary stimulus such as an audible "hum" may be used in conjunction with the lights to create an association between the "hum" and those brain wave patterns evoked by the lights. Over time, the primary stimulus may be removed and only the secondary stimulus may be used to evoke the brain wave patterns through effective conditioning. One advantage of this kind of conditioning is that less expensive and less complex equipment may be used by a sleeper at home over time to produce the "hum" and to monitor other secondary indicators of the sleeper's sleep stage after the sleeper has been conditioned for a time using more expensive monitoring and sensory stimulus equipment.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, and without limitation, it is expected that the methods disclosed herein are not limited for use with human sleepers, but would also work with animals having sleep problems.

The invention claimed is:

1. A method of guiding a sleep pattern of a sleeper, the method comprising:
   monitoring at least one physiological characteristic of a sleeper indicative of a current sleep stage of the sleeper;
   generating a sensory stimulus to lead the sleeper to a sleep stage different from the current sleep stage; and
   calibrating to the sleeper's sleep pattern by monitoring the physiological characteristic of the sleeper for at least one full sleep cycle prior to generating the sensory stimulus.

2. The method of claim 1, wherein calibrating to the sleeper's sleep pattern further comprises determining at least one physiological characteristic indicative of when the sleeper is changing from one sleep stage to another sleep stage.

3. A method of guiding a sleep pattern of sleeper, the method comprising:
   monitoring at least one physiological characteristic of a sleeper indicative of a current sleep stage of the sleeper;
   generating a sensory stimulus to lead the sleeper to a sleep stage different from the current sleep stage; and
   establishing a personalized sleeper profile including at least one data reference indicating a sensory stimulus setting for the sleeper and referencing that data reference when generating the sensory stimulus to lead the sleeper.

4. A method of guiding a sleep pattern of a sleeper, the method comprising:

monitoring at least one physiological characteristic of a sleeper indicative of a current sleep stage of the sleeper; and generating a sensory stimulus to lead the sleeper to a sleep stage different from the current sleep stage, wherein the at least one physiological characteristic monitored is indicative of a sleep stage associated with sleep apnea of the sleeper and the sensory stimulus generated is generated to lead the sleeper to a sleep stage not associated with the sleeper's sleep apnea.

5. A method of guiding a sleep pattern of a sleeper, the method comprising:

monitoring at least one physiological characteristic of a sleeper indicative of a current sleep stage of the sleeper; and generating a sensory stimulus to lead the sleeper to a sleep stage different from the current sleep stage, wherein the at least one physiological characteristic monitored is indicative of a sleep stage associated with sleepwalking by the sleeper and the sensory stimulus generated is generated to lead the sleeper to a sleep stage not associated with the sleeper's sleepwalking.

6. A method of guiding a sleep pattern of a sleeper, the method comprising:

monitoring at least one physiological characteristic of a sleeper indicative of a current sleep stage of the sleeper; and generating a sensory stimulus to lead the sleeper to a sleep singe different from the current sleep stage, wherein the at least one physiological characteristic monitored is indicative of a sleep stage associated with bedwetting by the sleeper and the sensory stimulus generated is generated to lead the sleeper to a sleep stage not associated with the sleeper's bedwetting.

7. A method of guiding a sleep pattern of a sleeper, the method comprising:

monitoring at least one physiological characteristic of a sleeper indicative of a current sleep stage of the sleeper; and generating a sensory stimulus to lead the sleeper to a sleep stage different from the current sleep stage, wherein the at least one physiological characteristic monitored is indicative of a sleep stage associated with nightmares of the sleeper and the sensory stimulus generated is generated to lead the sleeper to a sleep stage not associated with the sleeper's nightmare.

8. A method of guiding a sleep pattern of a sleeper between NREM and REM sleep, the method comprising:

monitoring at least one physiological characteristic of the sleeper indicative of NREM sleep;

generating a sensory stimulus having at least one characteristic configured to lead the sleeper to enter REM sleep;

monitoring the physiological characteristic to determine whether the sensory stimulus was effective to lead the sleeper to enter REM sleep; and establishing a personalized sleeper profile including at least one data reference indicating a sensory stimulus setting for the sleeper and referencing that data reference when generating the sensory stimulus to lead the sleeper.

9. A sleep pattern adjustor comprising:

a physiological characteristic monitor;

a sensory stimulus generator; and a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second sleep stage, wherein the processor is further configured to calibrate to the sleeper's sleep pattern by monitoring at least one physiological characteristic of the sleeper for at least a portion of a sleep cycle prior to the sensory stimulus generator generating sensory stimuli.

10. The sleep pattern adjustor of claim 9, wherein the processor is further configured to calibrate to the sleeper's sleep pattern by determining at least one physiological characteristic indicative of when the sleeper is changing between sleep stages.

11. A sleep pattern adjustor comprising:

a physiological characteristic monitor;

a sensory stimulus generator; and a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second sleep stage, wherein the processor is further configured to reference a personalized sleeper profile for the sleeper and generate sensory stimulus in accordance with the sleeper's personalized sleeper profile.

12. A sleep pattern adjustor comprising:

a physiological characteristic monitor;

a sensory stimulus generator; and a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second sleep stage, wherein the processor is configured to receive input indicative of a sleep stage associated with the sleeper experiencing sleep apnea and provide output to generate sensory stimulus in response to the input received to lead the sleeper to a different sleep stage not associated with the sleeper experiencing sleep apnea.

13. A sleep pattern adjustor comprising:

a physiological characteristic monitor;

a sensory stimulus generator; and a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second steep stage, wherein the processor is configured to receive input indicative of a sleep stage associated with the sleeper sleepwalking and provide output to generate sensory stimulus in response to the input received to lead the sleeper to a different sleep stage not associated with the sleeper sleepwalking.

14. A sleep pattern adjustor comprising:
a physiological characteristic monitor;
a sensory stimulus generator; and
a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second sleep stage, wherein the processor is configured to receive input indicative of a sleep stage associated with the sleeper wetting the bed and provide output to generate sensory stimulus in response to the input received to lead the sleeper to a different sleep stage not associated with the sleeper wetting the bed.

15. A sleep pattern adjustor comprising:
a physiological characteristic monitor;
a sensory stimulus generator; and
a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generator at least a first sensory stimulus in response to the input received from the physiological characteristic monitor to lead the sleeper from the first sleep stage to a second sleep stage, wherein the processor is configured to receive input indicative of a sleep stage associated with the sleeper having a nightmare and provide output to generate sensory stimulus in response to the input received to lead the sleeper to a different sleep stage not associated with the sleeper having a nightmare.

16. A sleep pattern adjustor comprising:
a physiological characteristic monitor;
a sensory stimulus generator; and
a processor operatively associated with the physiological characteristic monitor and the sensory stimulus generator, the processor configured to receive input from the physiological characteristic monitor indicative of a first sleep stage of a sleeper and provide output to the sensory stimulus generator to cause the sensory stimulus generator to generate at least a first sensory stimulus in response to the input received from the physiological characteristic monitor to lead the sleeper from the first sleep stage to a second sleep stage, wherein the processor is configured to store a personalized sleep profile and generate the sensory stimulus in accordance with data from the personalized sleep profile.

17. The sleep pattern adjustor of claim 16, wherein the personalized sleep profile comprises data indicative of the sleeper's sleep stages and data indicative of the stimuli to which the sleeper responds for pacing and leading the sleeper from the first sleep stage to the second sleep stage.

18. An apparatus for guiding a sleep pattern of a sleeper to change between NREM and REM sleep, the apparatus comprising:
a physiological characteristic monitor configured to monitor at least one physiological characteristic of a sleeper;
a sensory stimulus generator configured to generate at least one sensory stimulus in response to the physiological characteristic of the sleeper; and
a processor operatively associated with the physiological characteristic monitor and the sensory stimulus generator, the processor configured to receive input from the physiological characteristic monitor indicative of a NREM sleep stage, and provide output to the sensory stimulus generator to lead the sleeper to change to a REM sleep stage, wherein the processor is further configured to calibrate to the sleeper's sleep patterns and to calculate an optional sleep pattern related to an amount of time remaining in a preselected sleep period duration.

19. The apparatus of claim 18, wherein the processor is further configured to guide the sleeper through the optimal sleep pattern by causing the sensory stimulus generator to generate the at least one sensory stimulus responsive to the physiological characteristic of the sleeper to pace the sleeper, adjusting at least one characteristic of the sensory stimulus generated to lead the sleeper, and determine whether the sleeper is following the lead by monitoring the physiological characteristic of the sleeper through the physiological characteristic monitor.

20. An apparatus for guiding a sleep pattern of a sleeper to change between NREM and REM sleep, the apparatus comprising:
a physiological characteristic monitor configured to monitor at least one physiological characteristic of a sleeper;
a sensory stimulus generator configured to generate at least one sensory stimulus in response to the physiological characteristic of the sleeper; and
a processor operatively associated with the physiological characteristic monitor and the sensory stimulus generator, the processor configured to receive input from the physiological characteristic monitor indicative of a NREM sleep stage, and provide output to the sensory stimulus generator to lead the sleeper to change to a REM sleep stage, wherein the processor is further configured to reference a personalized sleeper profile for the sleeper and the sensory stimulus generator is configured to generate sensory stimulus in accordance with the sleeper's personalized sleeper profile.

* * * * *

UNITED STATES PATENT AND TRADEMARK OFFICE
CERTIFICATE OF CORRECTION

PATENT NO. : 7,041,049 B1
APPLICATION NO. : 10/718960
DATED : May 9, 2006
INVENTOR(S) : Raniere It is certified that error appears in the above-identified patent and that said Letters Patent is hereby corrected as shown below:

Column 8
Line 32, delete ";"

Column 15
Line 31, delete "singe" and insert -- stage --

Column 17
Line 37, delete "generator to generator" and insert -- generator to generate --

Column 18
Line 25, delete "optional" and insert -- optimal --

Signed and Sealed this

Twenty-second Day of August, 2006

JON W. DUDAS
*Director of the United States Patent and Trademark Office*